(12) United States Patent
Abair et al.

(10) Patent No.: US 12,332,025 B2
(45) Date of Patent: Jun. 17, 2025

(54) LUMBAR SUPPORT POUCH FOR BALLISTIC VEST

(71) Applicant: Terra Apparel, Inc., Comfort, TX (US)

(72) Inventors: Benjamin Alexander Abair, Comfort, TX (US); Kaegan McInturff, Comfort, TX (US); Seth Carlstrom, Bozeman, MT (US)

(73) Assignee: Terra Apparel, Inc., Comfort, TX (US)

( * ) Notice: Subject to any disclaimer, the term of this patent is extended or adjusted under 35 U.S.C. 154(b) by 58 days.

(21) Appl. No.: 18/187,646

(22) Filed: Mar. 21, 2023

(65) Prior Publication Data

US 2023/0296354 A1   Sep. 21, 2023

Related U.S. Application Data (60) Provisional application No. 63/322,160, filed on Mar. 21, 2022.

(51) Int. Cl.
*F41H 1/02*        (2006.01)
*A61F 5/02*        (2006.01)

(52) U.S. Cl.
CPC .............. *F41H 1/02* (2013.01); *A61F 5/028* (2013.01)

(58) Field of Classification Search
CPC ...... F41H 1/02; A45C 2011/007; A61F 17/00; A45F 3/06
See application file for complete search history.

(56) References Cited

U.S. PATENT DOCUMENTS

| | | | |
|---|---|---|---|
| 5,652,961 A | 8/1997 | Knight-Yurt | |
| 9,874,423 B1* | 1/2018 | Hughes | A41D 13/0012 |
| 11,647,818 B2* | 5/2023 | Marquez | A45C 5/065 |
| | | | 224/101 |
| 2006/0288466 A1* | 12/2006 | Bucheit | A41D 13/0012 |
| | | | 2/102 |
| 2008/0121730 A1* | 5/2008 | Calkin | A45F 3/06 |
| | | | 383/22 |
| 2011/0035855 A1 | 2/2011 | Gewant | |
| 2011/0204114 A1* | 8/2011 | Miller | A45F 3/06 |
| | | | 224/582 |
| 2014/0262851 A1* | 9/2014 | Adler | A45C 11/24 |
| | | | 29/428 |
| 2017/0307335 A1* | 10/2017 | Skifstad | F41C 33/041 |
| 2018/0160744 A1 | 6/2018 | Blauer | |
| 2020/0261286 A1* | 8/2020 | Evans | A45F 3/14 |
| 2022/0160556 A1* | 5/2022 | Evans | A45C 13/02 |

* cited by examiner

*Primary Examiner* — Katherine M Moran
(74) *Attorney, Agent, or Firm* — MORRISS O'BRYANT COMPAGNI CANNON, PLLC (57) ABSTRACT

A lumbar support pouch for a ballistics vest comprises an elongate pouch having a first open end and a second open end. A laterally extending tab is attached to an upper side of the elongate pouch and is configured to attach to a lower end of a ballistics vest. A first medical kit is inserted into and retained by the first pocket and has a first grasping strap extending from the first medical kit for grasping by a user. A second medical kit is inserted into and retained by the second pocket and has a second grasping strap extending from the second medical kit for grasping by a user. The pouch and medical kits form a lumbar support for a ballistics vest when attached thereto.

18 Claims, 13 Drawing Sheets

LUMBAR SUPPORT POUCH FOR BALLISTIC VEST

CROSS-REFERENCE TO RELATED APPLICATION

The present application claims priority to U.S. Provisional Patent Application Ser. No. 63/322,160 filed on Mar. 21, 2022, the entirety of which is incorporated by this reference.

BACKGROUND

Field of the Invention

The present invention relates generally to lumbar supports, more specifically, to a lumbar support containing a medical kit for a ballistic vest.

State of the Related Art

Ballistics vests, which are also referred to as bullet-proof vests, armored vests or plate carriers, typically comprise four main components: a chest panel, a back panel, shoulder straps that coupled the chest pad to the back pad over each shoulder and a cummerbund that extends to and between the front pad and the back pad proximate the lower portions of the front and back pads. The front and back panels include pockets to accommodate ballistic plates, which may typically range in size from 8"×10" to 11"×14". The shoulder straps are typically adjustable to allow adjustment of the front and back panels relative to one another so as to be able to adjust the height of the front and back panels relative to the chest and back of the wearer. The cummerbund may include release buckles at each side of the front and back panels to allow the sides of the vest to be released for placement and removal of the vest. In addition, the cummerbund portion may include a number of auxiliary pockets for holding various items depending on the primary application of the vest (e.g., combat, medical, security, etc.) For example, for military applications, the vest may include a number of pockets for storing ammunition magazine clips, a flashlight, a tourniquet, etc.

To allow for maximum freedom of movement while covering vital organs of users wearing a ballistic vest, the vests are typically configured to cover the chest and back of the user with the lower edge of the ballistic vest residing just below the rib cage. As a result of the thickness of the ballistic vest, a significant gap is formed between the bottom of the ballistic vest and bottom of the lower back of the wearer. When riding in a vehicle, for example, this gap creates a space between the lower back of the wearer and the back of the seat of the vehicle such that the lumbar region of the wearer's back is unsupported. Because the lumbar portion of the wearer's back is unsupported, the wearer can experience lower back pain, especially on long rides.

Furthermore, given the size and configuration of ballistics vests, there is often not enough room to store additional gear, such as field medical kits. Thus, there is a need in the art to provide a pouch configured to be attached to the bottom of the back panel of a ballistics vest that is configured to retain one or more field medical kits that are easily accessible and removable from the ballistics vest and that provides a lumbar support for the person wearing the ballistics vest.

The present invention is thus a significant improvement to ballistic vests and the like known in the art.

SUMMARY OF THE INVENTION

Accordingly, the present invention provides a lumbar support pouch for a ballistics vest comprising an elongate pouch divided into a first pouch and a second pouch of substantially equal size. The first pouch extends from a first side of the elongate pouch to a midpoint and the second pouch extends from the midpoint to a second side of the elongate pouch. The first side of the elongate pouch forms a first open end and the second side of the elongate pouch forms a second open end. A laterally extending flap is permanently attached along to and along an upper side of the elongate pouch and is configured to releasably attach to a lower end of a ballistics vest. A first medical kit is inserted into and retained by the first pouch and has a first grasping strap extending from the first medical kit. The first grasping strap extends from the first open end of the elongate pouch for grasping by a user. A second medical kit is inserted into and retained by the second pouch and has a second grasping strap extending from the second medical kit. The second grasping strap extends from the first open end of the elongate pouch for grasping by a user. The first and second pouches and corresponding first and second medical kits form a lumbar support along the bottom of the ballistics vest to which the lumbar support pouch is attached.

In one embodiment, a lumbar support pouch for a ballistics vest comprises an elongate pouch, the first side of the elongate pouch forming a first open end and the second side of the elongate pouch forming a second open end. A laterally extending tab is attached along and permanently attached to an upper side of the elongate pouch and is configured to be releasably attached to a lower end of a ballistics vest. A first medical kit is inserted into and retained by the first pocket and has a first grasping strap extending from the first medical kit. The first grasping strap extends from the first open end of the elongate pouch for grasping by a user to remove the first medical kit from the first pocket. A second medical kit is inserted into and retained by the second pocket and has a second grasping strap extending from the second medical kit, the second grasping strap extends from the second open end of the elongate pouch for grasping by a user to remove the second medical kit from the second pocket.

In another embodiment, the elongate pouch is divided into a first pocket and a second pocket of substantially equal size, the first pocket extending from a first side of the elongate pouch to a midpoint and the second pocket extending from the midpoint to a second side of the elongate pouch.

In another embodiment, the elongate pouch is comprised of a front panel sewn to a second panel and having a seam extending vertically along a midpoint of the elongate pouch to form the distal ends of the first and second pockets.

In still another embodiment, when the tab is attached to a lower end of a back of a ballistics vest, the lumbar support pouch is configured to reside proximate a lumbar region of a wearer of the ballistics vest.

In yet another embodiment, the first and second medical kits are each comprised of an elongate fabric panel having a back side and a front side, the front side having a plurality of medical supply retaining structures comprising at least one of a pocket and a bungee cord retaining system.

In still another embodiment, the first and second medical kits are each comprised of a first end portion having an elongate strap attached at one end thereto, the elongate strap having a first section of hook or loop tape attached to a back side thereof and a front side of the end portion having a second section of hook or loop tape attached thereto and configured for selective attachment to the first second of hook or loop tape.

In another embodiment, the elongate fabric panel is configured to be folded in half to form a folded end with the plurality of medical supply retaining structures positioned on an inside of the elongate fabric panel when folded.

In yet another embodiment, the first and second medical kits are configured to be inserted with the folded end first into the elongate pouch.

In still another embodiment, the first grasping strap of the first medical kit is attached to a second end portion of the elongate fabric panel of the first medical kit and the second grasping strap of the second medical kit is attached to a second end portion of the elongate fabric panel of the second medical kit.

In another embodiment, a ballistics vest comprises a front panel for holding a first ballistics plate, a back panel for holding a second ballistics plate, shoulder straps coupling the front panel to the back panel over shoulders of a wearer, and side straps for coupling the front panel to the back panel around the torso of the wearer. An elongate pouch has a first side that forms a first open end and a second side that forms a second open end. A laterally extending tab is attached along and permanently attached to an upper side of the elongate pouch and is configured to releasably attach to a lower end of the back panel of the ballistics vest. A first medical kit inserted into and retained by the first pocket and having a first grasping strap extending from the first medical kit, the first grasping strap extending from the first open end of the elongate pouch for grasping by a user to remove the first medical kit from the first pocket. A second medical kit is inserted into and retained by the second pocket and has a second grasping strap extending from the second medical kit, the second grasping strap extending from the second open end of the elongate pouch for grasping by a user to remove the second medical kit from the second pocket.

These and other aspects and advantages of the invention will become more apparent from the following detailed description thereof and the accompanying exemplary drawings.

DETAILED DESCRIPTION OF THE ILLUSTRATED EMBODIMENTS

Those of ordinary skill in the art will realize that the following description of the present invention is illustrative only and not in any way limiting. Other embodiments of the invention will readily suggest themselves to such skilled persons, including, without limitation, combinations of features of the illustrated embodiments.

Figure 1:
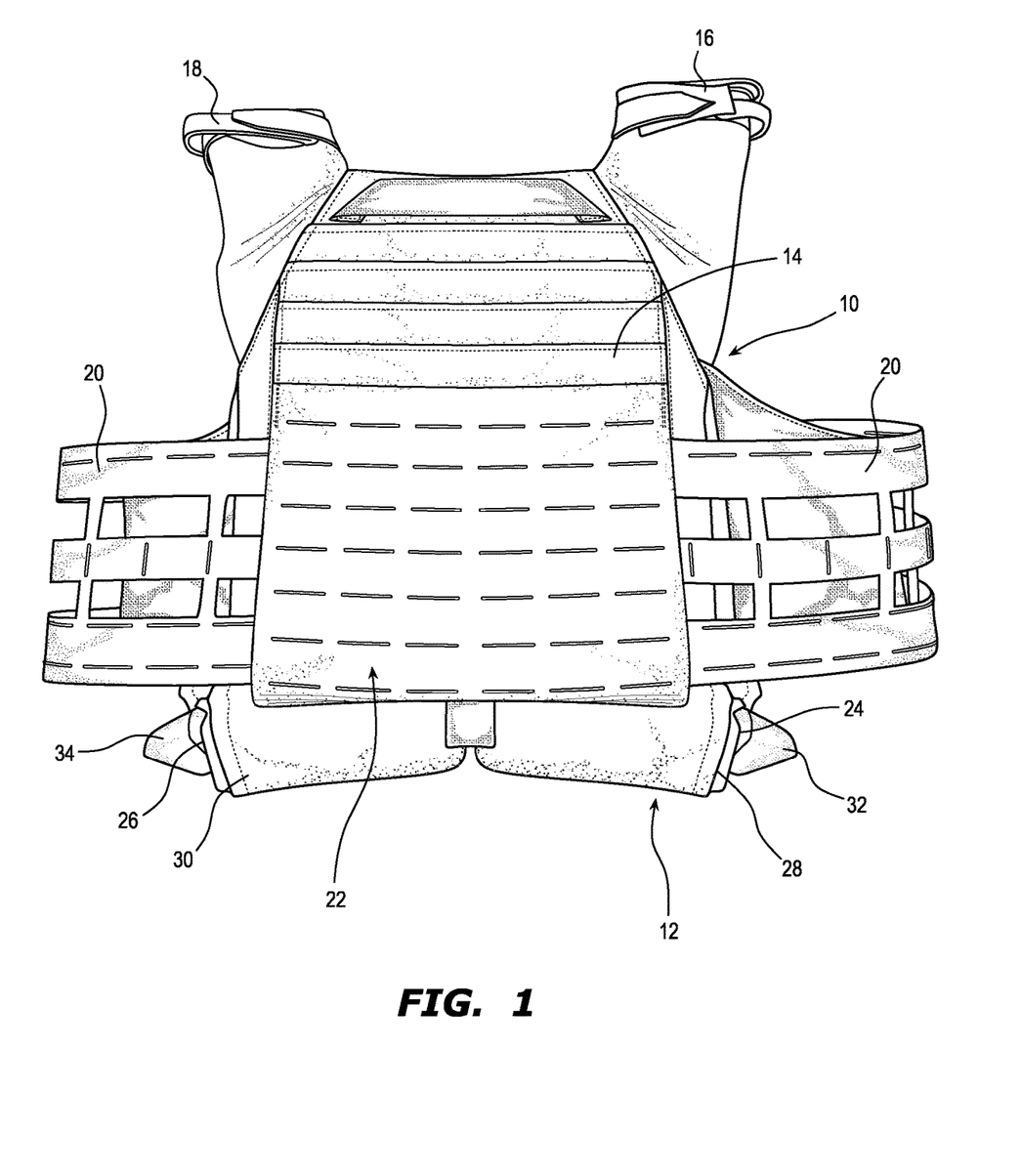
FIG. 1 is a back view of a ballistics vest with a lumbar support pouch in accordance with the principles of the present invention.

FIG. 1 illustrates a back view of a ballistics vest, generally indicated at 10, to which a laterally extending lumbar pouch, generally indicated at 12, is attached. The ballistics vest 10 includes a back panel 14, shoulder straps 16 and 18 and a cummerbund 20 integrated into the vest 10 and extending laterally around the sides of the vest 10.

The lumbar pouch 12 is attached to a lower end portion 22 of the back panel 14 and extends laterally and parallel to the lower end portion 22. In this embodiment, the lumbar pouch 12 is fitted with a pair of medical kits 24 and 26, with one of the medical kits 24 and 26 fitted within a respective side 28 and 30 of the lumbar pouch 12. Further, each medical kit 24 and 26 includes a grasping strap 32 and 34, respectively, each in the form of a loop, for grasping by the hand of a user to be able to easily and quickly locate and pull the medical kits 24 and 26 from the lumbar pouch 12 when needed. The lumbar pouch 12 is formed from fabric and may be the same fabric as that which forms the vest, including the same color and camouflage pattern, or may be comprised of other materials known in the art.

Figure 2:
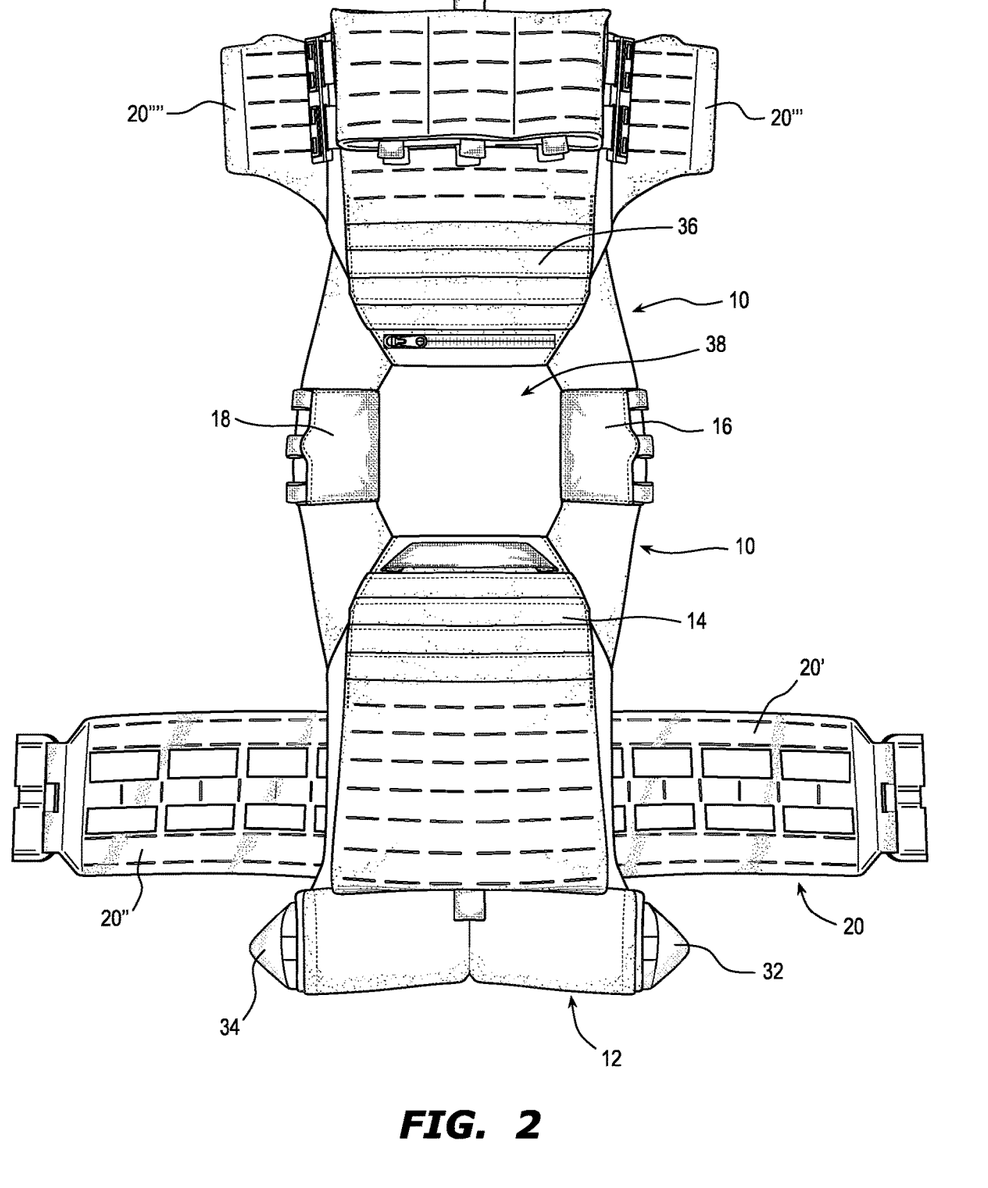
FIG. 2 is a plan view of the ballistics vest with lumbar support pouch illustrated in FIG. 1.

As shown in FIG. 2, a front panel 36 is attached to the back panel 14 with the shoulder straps 18, thereby forming an aperture 38 therein between for fitting over a user's head when placing the ballistics vest 10 on the user. When placed over the user, the front panel 36 resides over the chest of the user and the back panel 14 resides over the back of the user. The integrated cummerbund 20 includes back portions 20' and 20" and front portions 20" and 20". The free end of portion 20' is configured to be coupled to the free end of portion 20" and the free end of portion 20" is configured to be coupled to the free end of portion 20" in order to secure the front and back panels 36 and 14 together and around the ribcage of the user. The lumbar pouch 12 resides below the back panel 14 and the cummerbund portions 20' and 20" and has an overall width that may be greater than a corresponding adjacent width of the back panel 14 as shown. The width of the lumbar pouch 12 and thus the position of the grasping straps 32 and 34 is such that the grasping straps 32 and 34 are positioned closer to the sides of the users lower back so as to be easily reached and grabbed by the user without having to remove or laterally manipulate the vest 10.

Figure 3:
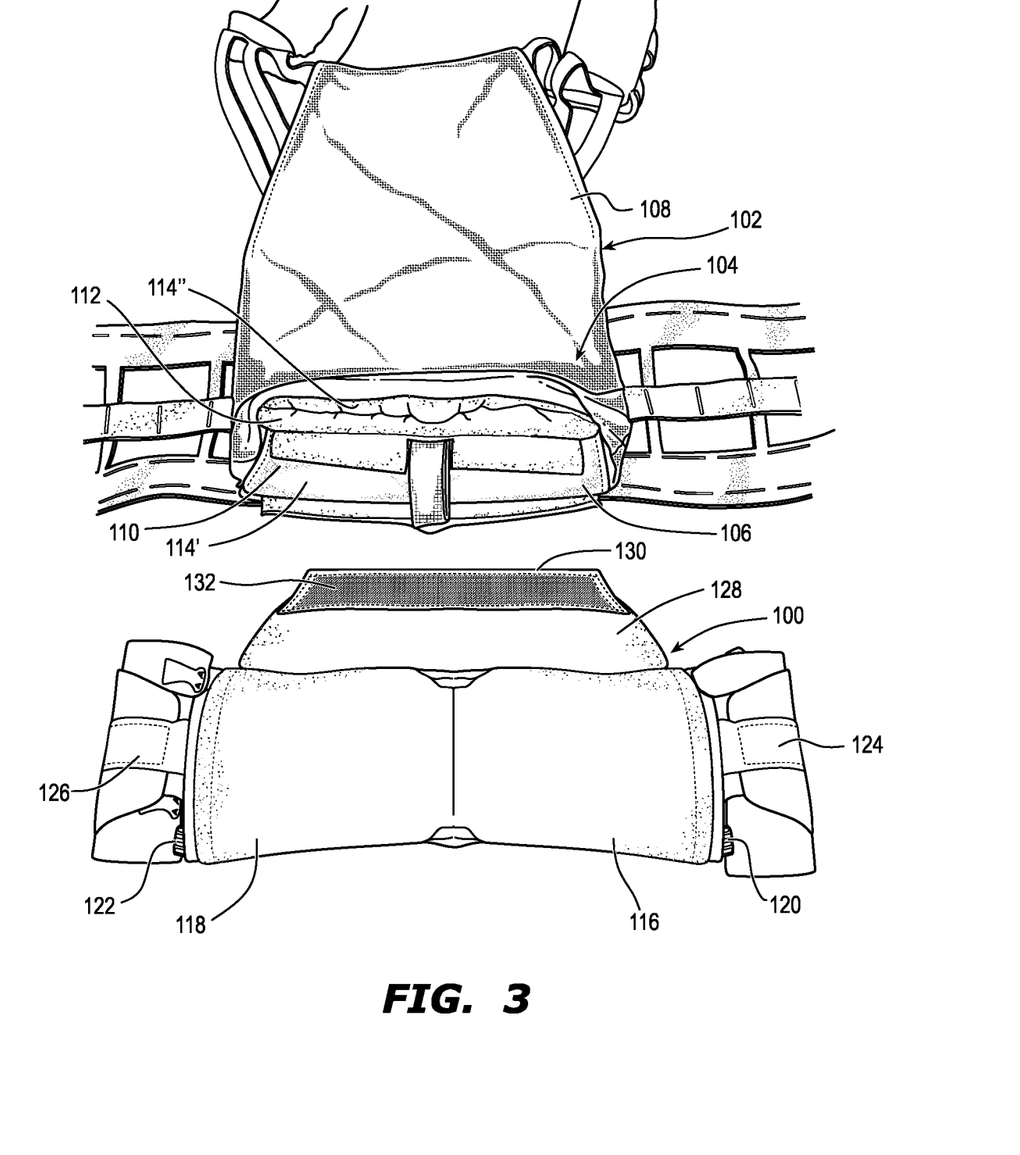
FIG. 3 is a front view of a back panel of the ballistics vest illustrate in FIG. 1 and a back view of the lumbar support pouch illustrated in FIG. 1 detached from the back panel.
Figure 4:
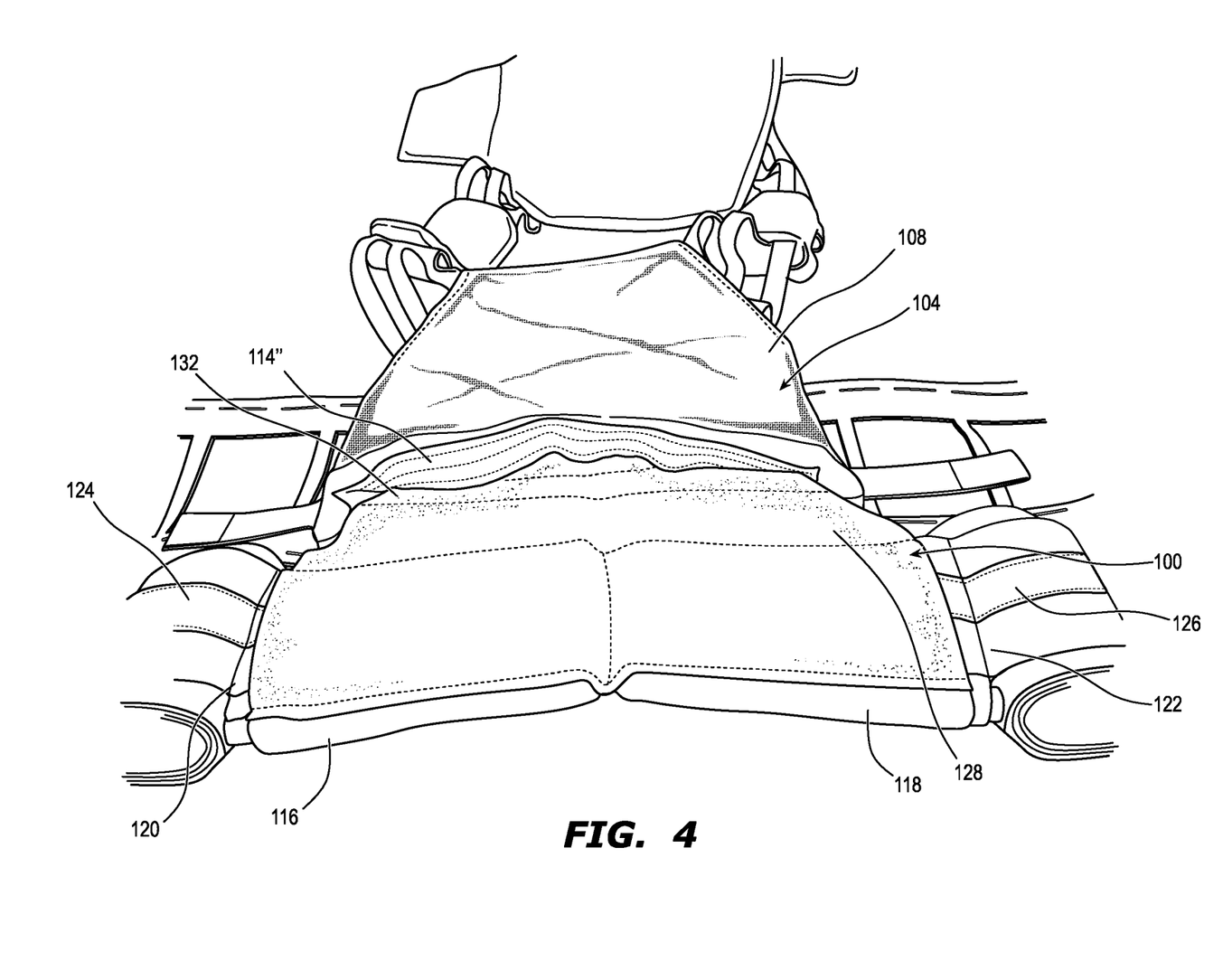
FIG. 4 is a front view of the back panel of the ballistics vest and the lumbar support panel partially attached to the back panel illustrated in FIG. 1.

As shown in FIGS. 3 and 4, a lumbar pouch 100, in accordance with the present invention, is configured to be attachable and removable from an existing ballistics vest 102 without the need to modify the ballistics vest 102. The back panel 104 of the ballistics vest 102 is comprised of a front panel section 106 and a back panel section 108 and forming a pocket 110 therein between. The pocket 110 is configured to receive and hold a ballistics plate 112 therein. The lower ends of the front panel and back panel sections are provided with hook and loop tape 114' and 114" in order to secure the lower ends together and retain the ballistics plate 112 within the back panel 104.

The lumbar pouch 100 includes a pair of laterally extending pockets 116 and 118, each having a closed end proximate a midpoint or center of the lumbar pouch 100, an open end along a respective lateral side of the lumber pouch, and sized to receive and retain a respective medical kit 120 or 122. In addition, straps 124 and 126 are permanently attached to the medical kits 120 and 122, respectively, and form sleeves securable by hook and loop tape (not visible) around an Ace® bandage as shown. In this embodiment, in order to remove a medical kit 120 or 122 from the lumbar pouch 100, a user can simply grab around one of the straps 124 and 128 and corresponding Ace® bandage and pull the corresponding medical kit 120 and 122 from a respective pocket 116 and 118. The pockets 116 and 118 are sized and shaped to hold the medical kits 120 and 122 therein by friction fit, but could also be retained by hook and loop tape or other mechanisms that allows the medical kits 120 and 122 to be easily and quickly removed from the lumbar pouch 100 when needed.

The upper portion of the lumbar pouch 100 includes an attachment flap 128 that extends laterally along the lumbar pouch 100 and is permanently attached thereto. The upper edge 130 of the flap 128 is provided with corresponding hook and loop tape (only hook and loop tape 132 being visible) to connect to the hook and loop tape 114' and 114" along the lower edges of the front and back panel sections 104 and 106. When being attached, as shown in FIG. 4, the hook and loop tape 114" mates with the hook and loop tape 132 of the flap 130 and the hook and loop tape 114' mates with corresponding hook and loop tape (not visible) on the opposite side of the flap 128 along the edge 130. When fully secured, the flap 128 is effectively sandwiched between and held in place relative to the front 106 and back 108 panel sections with the combination of hook and loop sections holding the ballistics plate 112 within the back panel 104.

Figure 5:
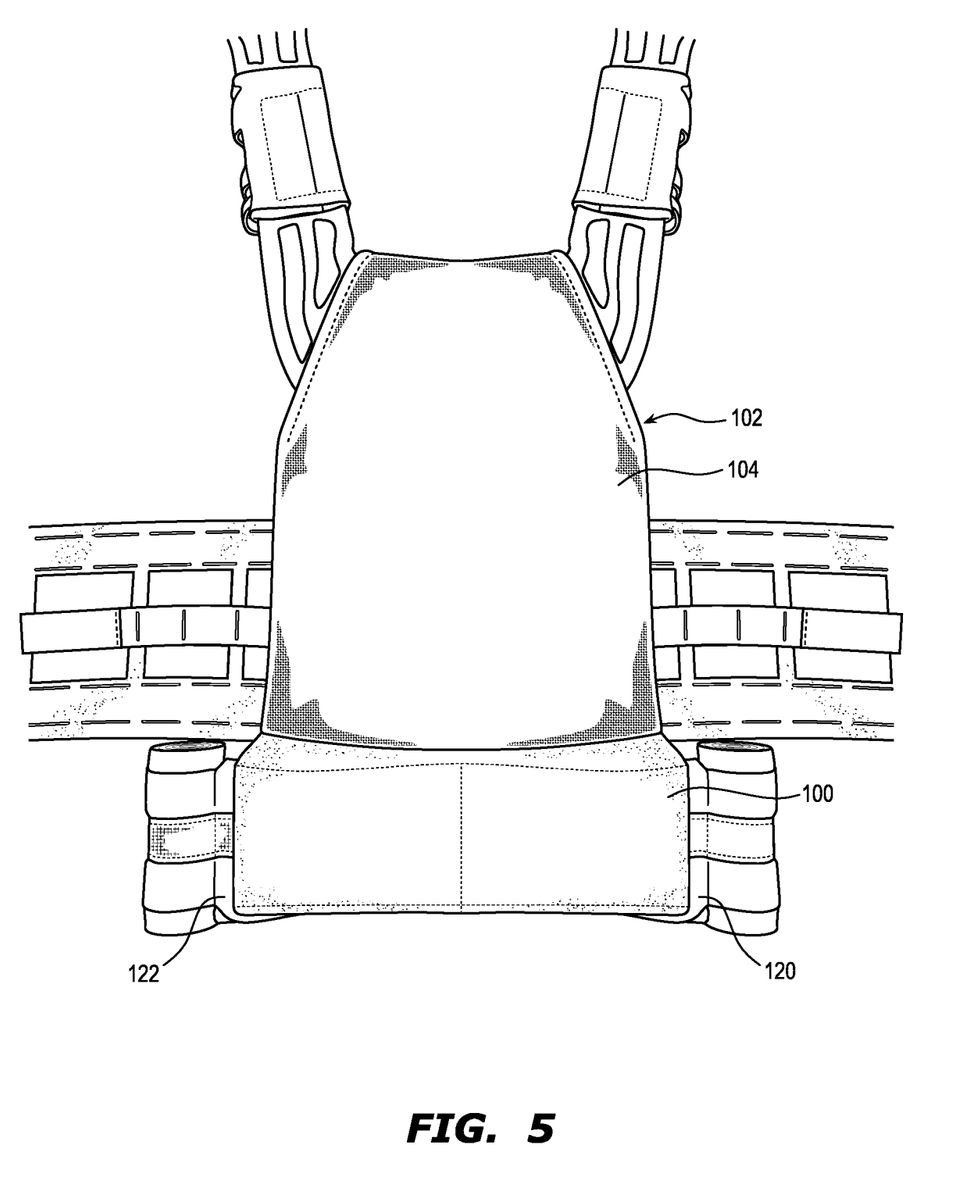
FIG. 5 is a front view of the back panel of the ballistics vest and the lumbar support panel illustrated in FIG. 1.

As shown in FIG. 5, when the lumbar pouch 100 is secured to the back panel 104 of the ballistics vest 102, the lumbar pouch 100 hangs from the bottom of the back panel 104 and extends laterally across the bottom edge of the back panel 104. The lumbar pouch 100 when loaded with the two medical kits 120 and 122 have a width and thickness that provide lumbar support for the user wearing the ballistics vest 102 between the users lower back and a seat back of a seat or chair upon which the user is sitting. That is, the thickness from front to back of the lumbar pouch 100 when loaded with medical kits 120 and 122 is of a similar thickness to the back panel 104 when loaded with a ballistics plate and thus forms a lumbar support for the user wearing the ballistics vest 102. Of course, the lumbar pouch 100 could be permanently attached to the ballistics vest as by sewing the upper flap to the bottom end of the back panel.

Figure 6A:
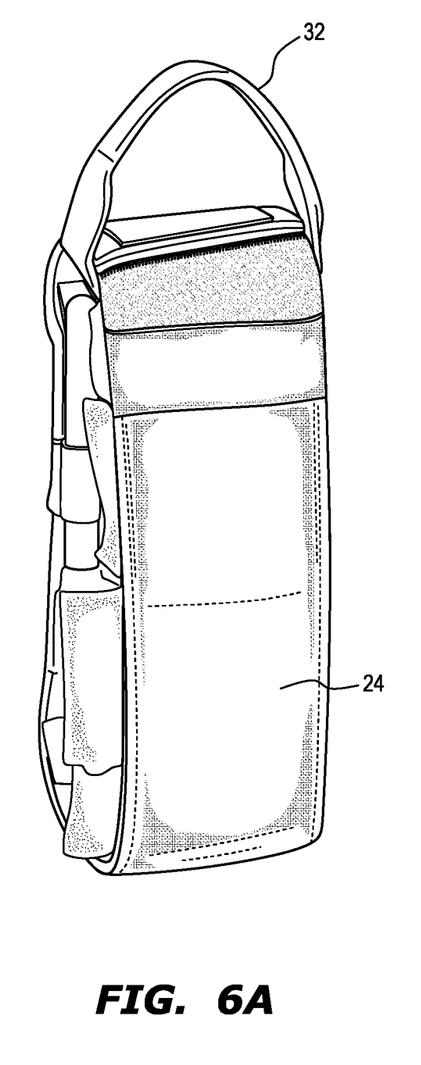
FIGS. 6A and 6B are front and inside views of a first embodiment of a medical kit for use with the ballistics vest with lumbar support pouch according to the present invention.
Figure 6B:
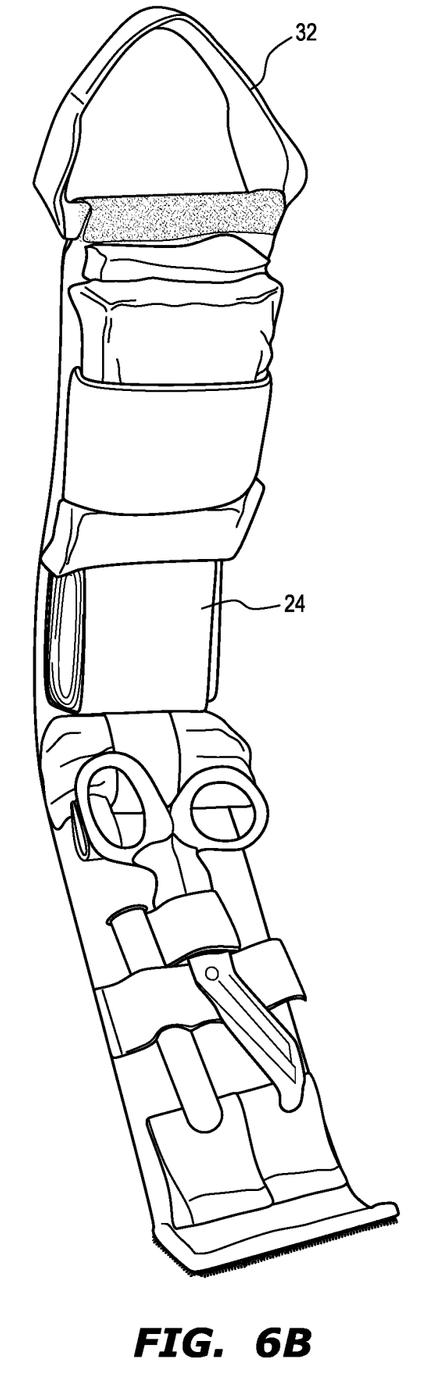
Figure 7A:
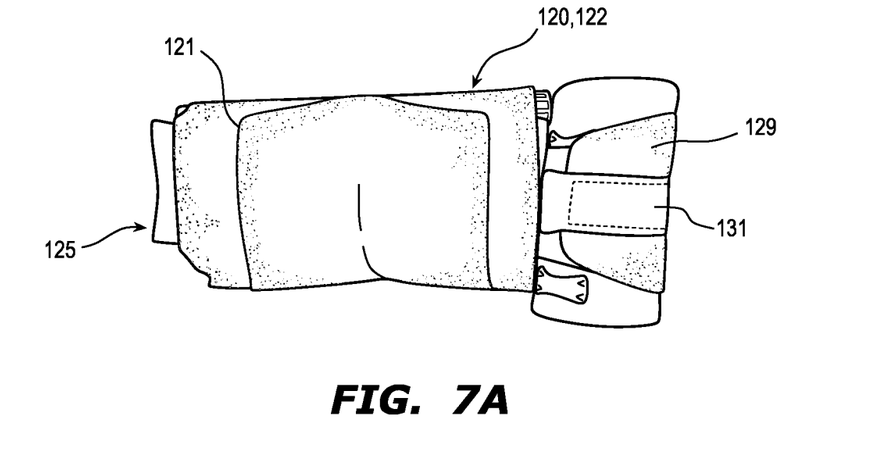
FIGS. 7A, 7B and 7C are front, back and inside views of a second embodiment of a medical kit for use with the ballistics vest with lumbar support pouch according to the present invention.
Figure 7B:
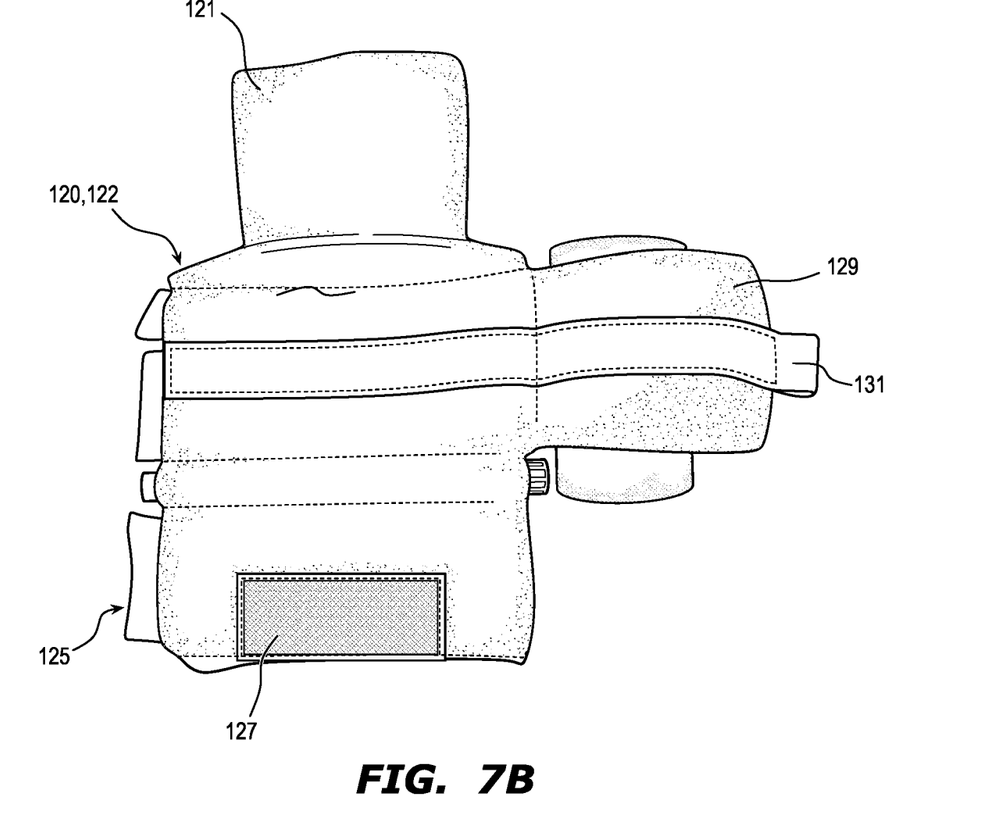
Figure 7C:
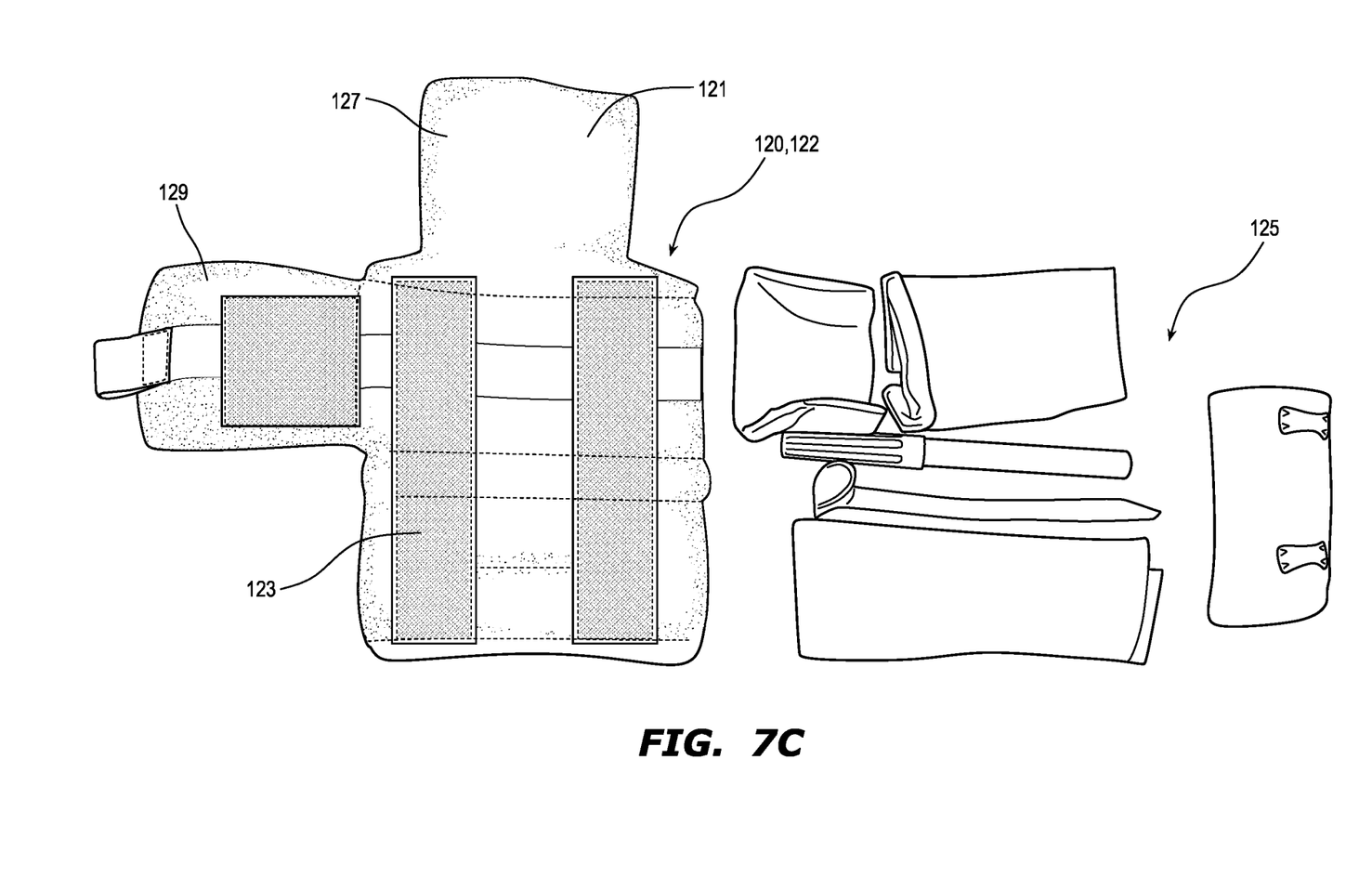

The medical kits 24 and 26 as shown with reference to FIG. 1, may comprise for example an IFAK medical kit as shown in FIGS. 6A and 6B. The medical kit 24 can be unfolded to reveal and access various medical supplies such as nitrile gloves, compressed gauze, bandages, a chest seal, a decompression needle, a nasopharyngeal airway w/lube, an aluminum eye shield, EMT Shears, a permanent marker, duct tape, etc. The permanently attached grasping strap 32 may be made red in color for easy visual identification and is sized to be easily grasped by the user in order to grasp and pull the medical kit 24 from its pocket of the lumbar pouch of the present invention.

The medical kits 120 and 122 as shown with reference to FIGS. 3, 4 and 5, may each comprise for a medical kit 120, 122 as shown in FIGS. 6A and 6B. The medical kit 120, 122 is comprised of a foldable fabric panel 121 having a plurality of straps 123 forming sleeves on an interior side configured to hold various medical supplies 125. The panel 121 is configured to be rolled around the medical supplies 125 and attached to itself with a hook and loop fastener 127. The panel 121 includes a laterally extending side portion 129 configured to wrap around and retain an Ace® bandage therein. A colored band 131, such as a red length of fabric strap, is permanently attached to and longitudinally extends over the outer surface and around the side portion 129 to identify the kit 120-122 as a medical kit. The kit 120, 122 can be unfolded to reveal and access the various medical supplies 125 such as combat gauze, a decompression needle, an airway tube, Ace® bandage, etc. As noted above, to remove the medical kit 120, 122 from the from its pocket of the lumbar pouch herein described, a user can grab the portion 129 holding the Ace® bandage and pull the medical kit 120, 122 from its pocket.

Figure 8A:
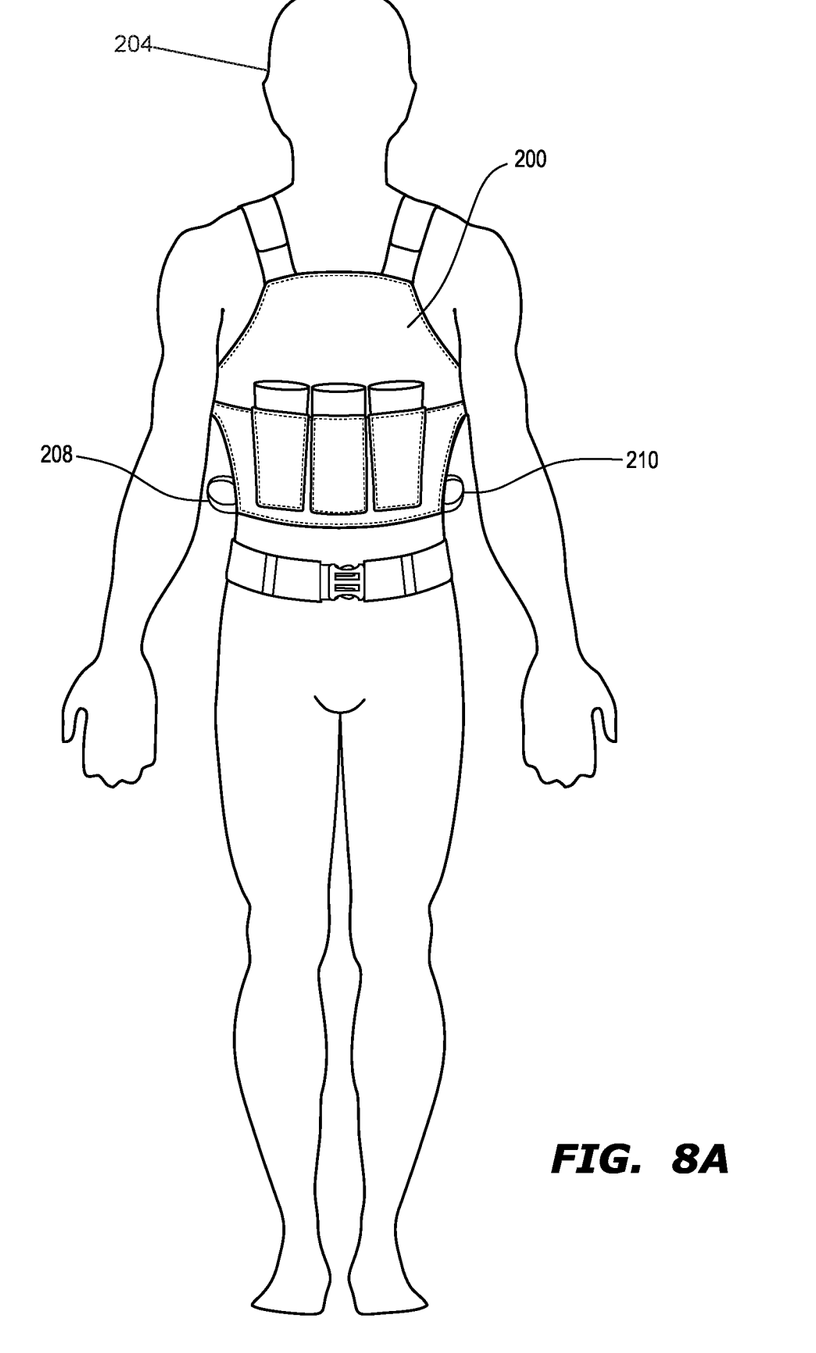
FIG. 8A is front side and back view of a user wearing a ballistics vest with a lumbar support pouch according to the present invention.
Figure 8B:
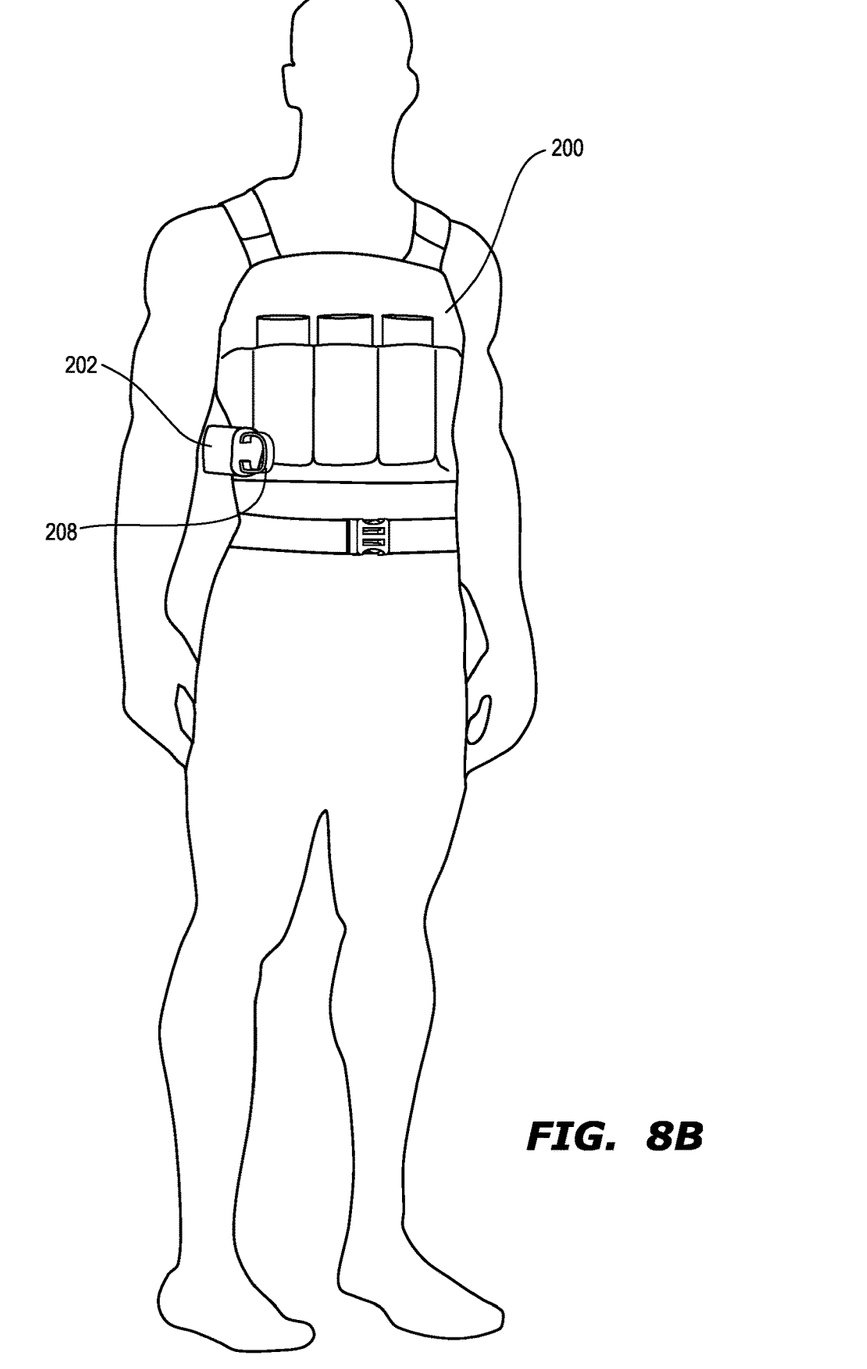
FIG. 8B is front side and back view of a user wearing a ballistics vest with a lumbar support pouch according to the present invention.
Figure 8C:
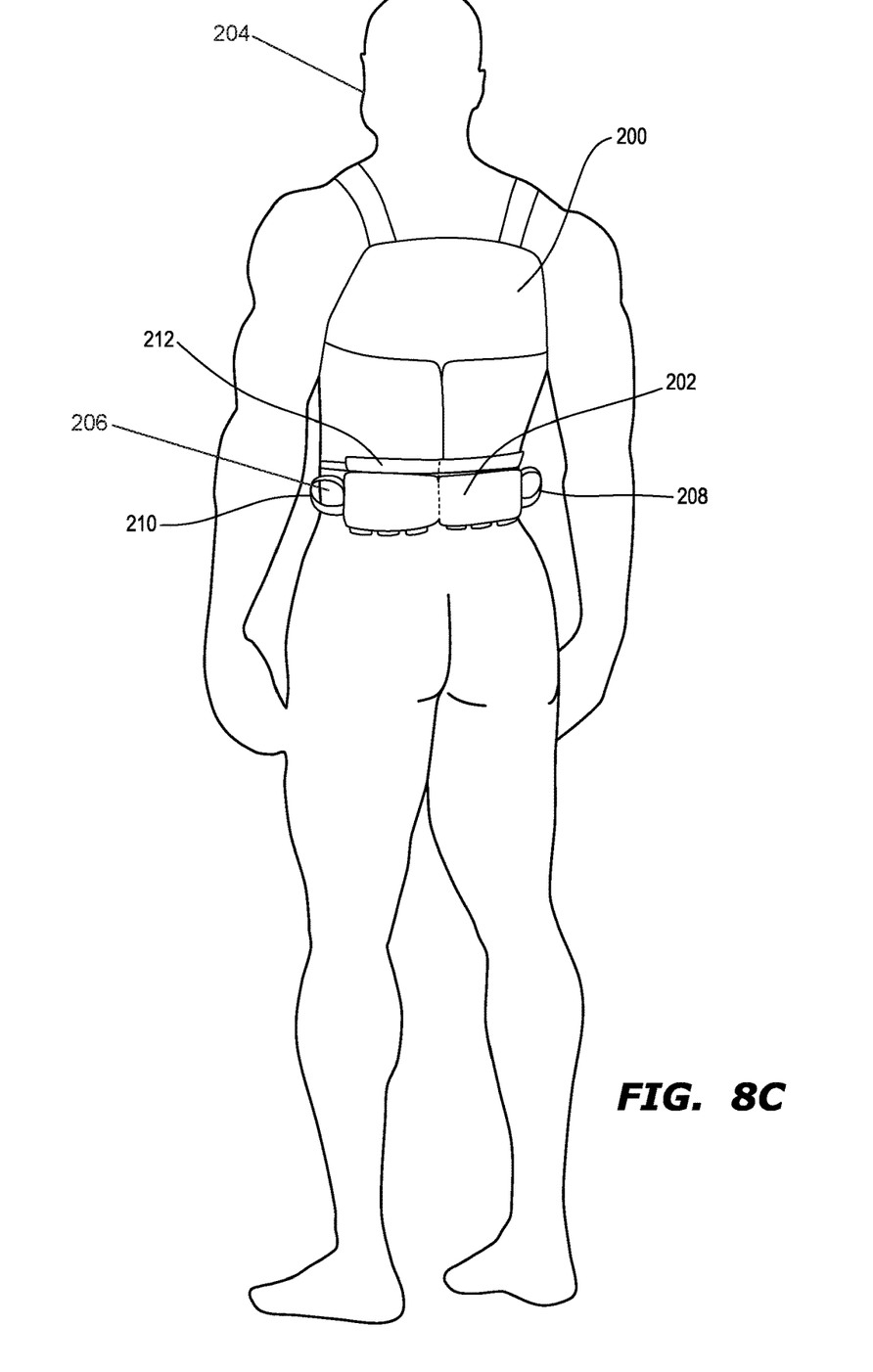
FIG. 8C is a back side view of a user wearing a ballistics vest with a lumbar support pouch according to the present invention.

FIGS. 8A, 8B and 8C show a ballistics vest 200 and a lumbar support pouch 202 of the present invention worn by a user 204. The lumbar support pouch 202 extends laterally along the lower back 206 of the user 204 with the strap handles 208 and 210 positioned at the sides of the user's torso for ease of grasping the straps 208 and 210 by hand. The lumber support pouch 202 is spaced from the lower end of the ballistics vest 200 by the attachment flap 212 that is permanently attached to the lumbar support pouch 202 and is removably attached to the ballistics vest 200 as previously described herein.

Figure 9:
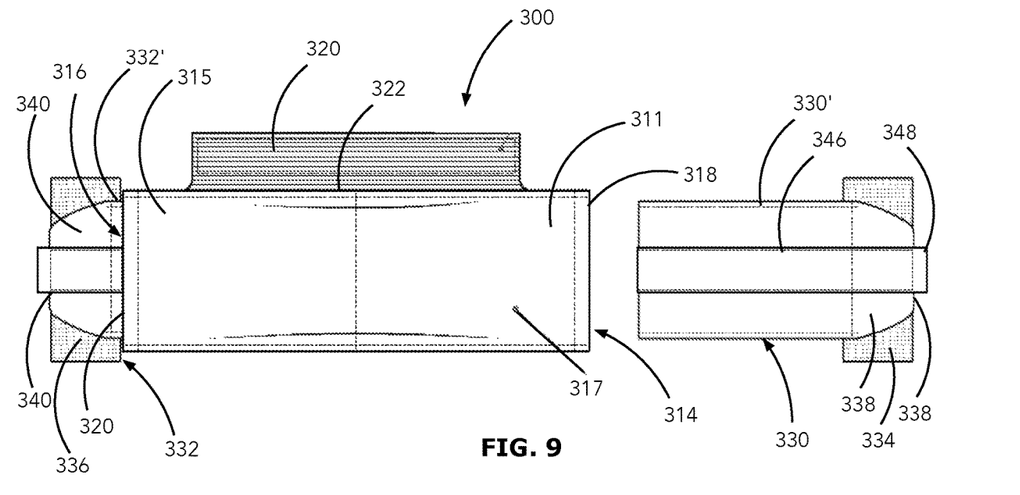
FIG. 9 is a back side view of another embodiment of a ballistic vest lumbar pouch according to the principles of the present invention.
Figure 10:
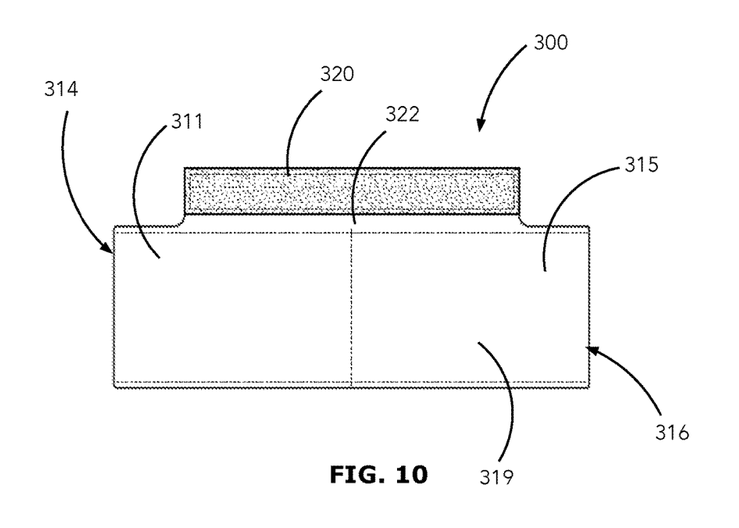
FIG. 10 is a back side view of the lumbar pouch according to the present invention illustrated in FIG. 9.

Referring now to FIGS. 9 and 10, there is illustrated another embodiment of a lumbar pouch, generally indicated at 300, according to the principles of the present invention. The lumbar pouch 300 is configured to attach to a lower end portion of the back panel of a ballistic vest, such as the ballistic vest 10 shown in FIG. 1, and to laterally extend along the lower end of the back of the ballistic vest 10 and parallel thereto so as to rest in the lumbar region of a user wearing the ballistic vest. Thus, when the user wears a ballistic vest with the lumbar pouch 300 attached thereto and sits in a chair or seat having a back rest, the lumbar pouch provides lumbar support for the lumbar region of the user's lower back. The lumbar pouch 300 includes a pair of pockets 311 and 315 with the pouch openings 314 and 316 on the lateral ends or sides 318 and 320, respectively of the pouch 300. The pockets 311 and 315 each form approximately 50% of the pouch 300 and thus dividing the pouch 300 in half and are formed in the pouch 300 by sewing seams into the pouch, which is formed from a rectangular front panel 317 sewn to a rectangular back panel 319 (see FIG. 10). The pouch 300 itself may be formed from a durable fabric, such as TWEAVE DURASTRECH, which is comprised of a SPANDEX/nylon blend with SPANDEX content ranging from 10-50%.

An elongate tab 320 extends along at least a top portion of the top edge 322 of the pouch 300 and may be integrally formed with the pouch 300. The tab 320 includes a strip of hook or loop tape (or combination hook and loop tape) to mate with the opposite and similarly sized and oriented hook or loop tape (or combination hook and loop tape) extending along the bottom edge of the ballistic vest. Thus, the pouch 312 can be attached to and essentially hung from the bottom edge of the ballistic vest in a manner that positions the pouch 300 proximate the lumbar region of the user or wearer of the ballistic vest, such as a Crye Precision JPC 2.0 armor vest.

The pockets 311 and 315 are configured and sized to receive medical kits 330 and 332, respectively, one medical kit 330 or 332 in each pocket 311 or 315. The medical kits 330 and 332 are comprised of a body portion 330' and 332', respectively, with the body portions 330' and 332' sized in length to fit within the respective pocket 311 or 315. ACE bandage wraps 334 and 336 are secured to the proximal ends 38 and 40, respectively, of each medical kit 330 and 332 with a strap 342 and 344, respectively, that wraps around the bandage wrap and secures it to the medical kit 330 or 332. The effective circumferential sized of each medical kit 330 and 332 is such that it forms a relatively tight friction fit within its respective pocket 311 or 315 so as to secure the medical kits 330 and 332 within the pouch 300. The back of each medical kit is provided with an elongate strap 346 that extends the length of the medical kit and may be red in color so as to be readily identifiable to a third party as a medical kit. The proximal end of the elongate strap 346 forms a loop 348 for grasping by the user. To remove a medical kit 330 or 332 from the pouch 300, the user can grab the pull tab formed by the loop 348 of the strap 346 and slide the medical kit from the pouch 300.

Figure 11:
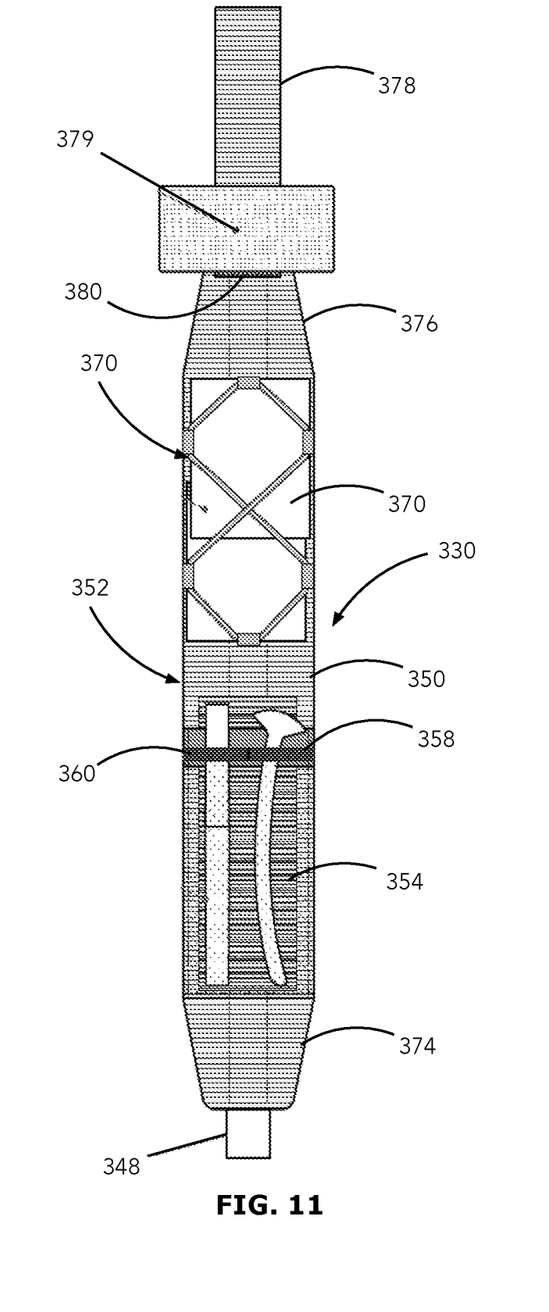
FIG. 11 is a front side view of a third embodiment of a medical kit for use with the ballistics vest with lumbar support pouch according to the present invention.
Figure 12:
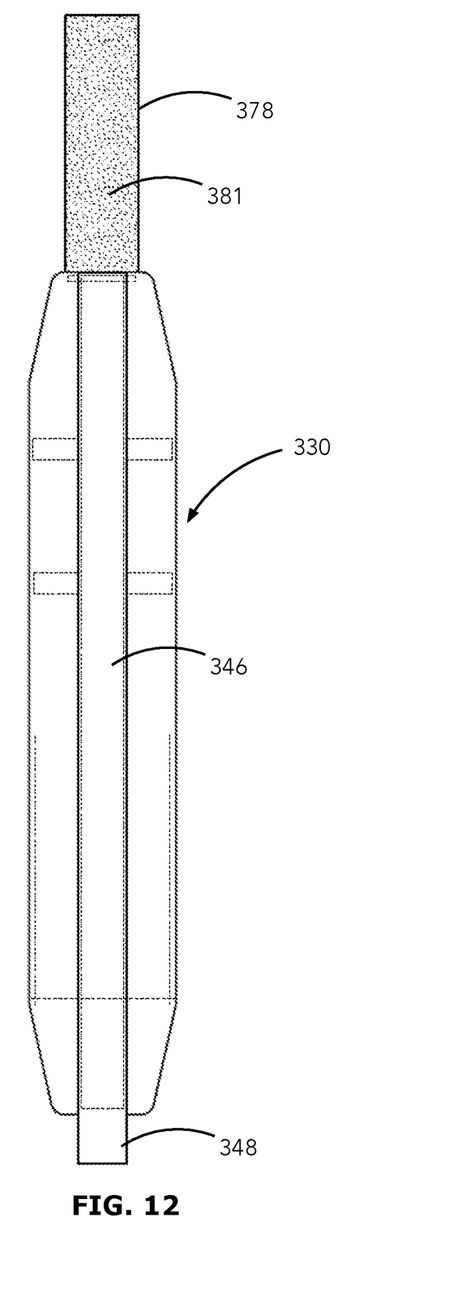
FIG. 12 is a back side view of the medical kit illustrated in FIG. 11 according to the present invention.

As shown in FIGS. 11 and 12, each medical kit, such as medical kit 30 is comprised of an elongate fabric panel 350 having various pockets and other attachment and retention features for holding a plurality of medical devices, tools, bandages and other medical supplies as may be desirable. The fabric panel 350 has a central rectangular section 352 having a pocket formed from a mesh panel 354 forming a one way pocket 356 that opens toward the center of the panel 350. The top end 358 of the pocket includes an elastic closure band 360 to help retain objects within the pocket 356. Such objects may include a pharyngeal tube, a decompression needle, a chest seal, gauze and/or other medical supplies. The other half of the central rectangular section 352 is provided with a crisscrossed bungee cord retention system 370 for holding a plurality of QUICKCLOT bandages 372 or other bandages or medical supplies as may be desired. The ends 374 and 376 of the panel 350 are tapered from the central rectangular section 352. One end 374 is provided with a wrap 378 configured to wrap around the ACE bandage 379 and secure it to the end 374 of the panel 350 with the ACE bandage 379 positioned transversely to the long axis of the panel 350 and the wrap 378. The back side 381 of the wrap 378 is provided with hook tape so that the ACE bandage 379 can be rolled up within the wrap 378 and the back side of the wrap 378 can attach to the section of hook tape 380 attached to the end 374 of the panel 350. Again, as previously noted, the back side of the panel 350 is provided with a colored band or strap 346 that forms the loop 348 for grasping by the user. To insert the medical kit 330 into the pouch 312 shown in FIG. 9, the panel 350 is folded in half with the medical supplies positioned within the interior of the medical kit 330 when folded. The folded end is then inserted into a respective pocket of the pouch 312. The combination of the fabric forming the pouch and the panel 350, which forms the back of the medical kit 330, forms a sufficiently padded lumbar support for the wearer of the ballistic vest when the pouch with two medical kits are inserted into the pouch and the pouch is attached to the ballistic vest and positioned proximate the lumbar region of the user.

While shown as being adapted to be attached to a lower end of a ballistics vest, the lumbar pouch as shown in the various embodiments herein could be adapted to be attached to other devices that include portions worn on the back of a user, such as to a bottom portion of a backpack or the like.

While the lumbar pouch for a ballistic vest of the present invention has been described with reference to a particular embodiment, those of skill in the art will appreciate that other similarly configured embodiments will readily suggest themselves upon an understanding of the principles of the present invention. Thus, the present invention of a lumbar support pouch and the appended claims are not limited to the features of the specific embodiments. For example, the lumbar support pouch for a ballistics vest could be configured to have a different overall shape, size or construction but still be within the scope of the claims.

Accordingly, the illustrated embodiments of this invention are not limited to any particular individual feature disclosed here, but include combinations of them distinguished from the prior art in their structures, functions, and/or results achieved. Features of the invention have been broadly described so that the detailed descriptions that follow may be better understood, and in order that the contributions of this invention to the arts may be better appreciated. Those skilled in the art who have the benefit of this invention, its teachings, and suggestions will appreciate that the concepts of this disclosure may be used as a creative basis for designing other structures, methods and systems for carrying out and practicing the present invention.

While there have been described various embodiments of the present invention, those skilled in the art will recognize that other and further changes and modifications may be made thereto without department from the spirit of the invention, and it is intended to claim all such changes and modifications that fall within the true scope of the invention. It is also understood that, as used herein and in the appended claims, the singular forms "a," "an," and "the" include plural reference, unless the context clearly dictates otherwise.

Unless defined otherwise, all technical and scientific terms used herein have the same meanings as commonly understood by one of ordinary skill in the art to which this invention belongs. While various methods and structures of the present invention are described herein, any methods or structures similar or equivalent to those described herein may be used in the practice or testing of the present invention. All references cited herein are incorporated by reference in their entirety and for all purposes. In addition, while the foregoing advantages of the present invention are manifested in the illustrated embodiments of the invention, a variety of changes can be made to the configuration, design and construction of the invention to achieve those advantages including combinations of components of the various embodiments. Hence, reference herein to specific details of the structure and function of the present invention is by way of example only and not by way of limitation.

What is claimed:

1. A lumbar support pouch for a ballistics vest, comprising:
   an elongate pouch, a first side of the elongate pouch forming a first open end and a second side of the elongate pouch forming a second open end;
   a laterally extending tab attached along and permanently attached to an upper side of the elongate pouch and configured to releasably attach to a lower end of a ballistics vest;
   a first medical kit inserted into and retained by a first pocket and having a first grasping strap extending from the first medical kit, the first grasping strap extending from the first open end of the elongate pouch for grasping by a user to remove the first medical kit from the first pocket; and a second medical kit inserted into and retained by a second pocket and having a second grasping strap extending from the second medical kit, the second grasping strap extending from the second open end of the elongate pouch for grasping by a user to remove the second medical kit from the second pocket.

2. The lumbar support pouch of claim 1, wherein the elongate pouch is divided into the first pocket and the second pocket of substantially equal size, the first pocket extending from the first side of the elongate pouch to a midpoint and the second pocket extending from the midpoint to the second side of the elongate pouch.

3. The lumbar support pouch of claim 2, wherein the elongate pouch is comprised of a front panel sewn to a second panel and having a seam extending vertically along the midpoint of the elongate pouch to form the distal ends of the first and second pockets.

4. The lumbar support pouch of claim 3, wherein when the tab is attached to a lower end of a back of a ballistics vest, the lumbar support pouch is configured to reside proximate a lumbar region of a wearer of the ballistics vest.

5. The lumbar support pouch of claim 1, wherein the first and second medical kits are each comprised of an elongate fabric panel having a back side and a front side, the front side having a plurality of medical supply retaining structures comprising at least one of a pocket and a bungee cord retaining system.

6. The lumbar support pouch of claim 5, wherein the first and second medical kits are each comprised of a first end portion having an elongate strap attached at one end thereto, the elongate strap having a first section of hook or loop tape attached to a back side thereof and a front side of the end portion having a second section of hook or loop tape attached thereto and configured for selective attachment to the first section of hook or loop tape.

7. The lumbar support pouch of claim 5, wherein the elongate fabric panel is configured to be folded in half to form a folded end with the plurality of medical supply retaining structures positioned on an inside of the elongate fabric panel when folded.

8. The lumbar support pouch of claim 7, wherein the first and second medical kits are configured to be inserted with the folded end first into the elongate pouch.

9. The lumbar support pouch of claim 8, wherein the first grasping strap of the first medical kit is attached to a second end portion of the elongate fabric panel of the first medical kit and the second grasping strap of the second medical kit is attached to a second end portion of the elongate fabric panel of the second medical kit.

10. A ballistics vest, comprising:
a front panel for holding a first ballistics plate, a back panel for holding a second ballistics plate, shoulder straps coupling the front panel to the back panel and configured to extend over shoulders of a wearer, and side straps for coupling the front panel to the back panel around the torso of the wearer;
an elongate pouch, a first side of the elongate pouch forming a first open end and a second side of the elongate pouch forming a second open end;

a laterally extending tab attached along and permanently attached to an upper side of the elongate pouch and configured to releasably attach to a lower end of the back panel of the ballistics vest;

a first medical kit inserted into and retained by a first pocket and having a first grasping strap extending from the first medical kit, the first grasping strap extending from the first open end of the elongate pouch for grasping by a user to remove the first medical kit from the first pocket; and a second medical kit inserted into and retained by a second pocket and having a second grasping strap extending from the second medical kit, the second grasping strap extending from the second open end of the elongate pouch for grasping by a user to remove the second medical kit from the second pocket.

11. The ballistics vest of claim 10, wherein the elongate pouch is divided into the first pocket and the second pocket of substantially equal size, the first pocket extending from the first side of the elongate pouch to a midpoint and the second pocket extending from the midpoint to the second side of the elongate pouch.

12. The ballistics vest of claim 11, wherein the elongate pouch is comprised of a front panel sewn to a second panel and having a seam extending vertically along the midpoint of the elongate pouch to form the distal ends of the first and second pockets.

13. The ballistics vest of claim 12, wherein when the tab is attached to a lower end of a back of a ballistics vest, the lumbar support pouch is configured to reside proximate a lumbar region of a wearer of the ballistics vest.

14. The ballistics vest of claim 10, wherein the first and second medical kits are each comprised of an elongate fabric panel having a back side and a front side, the front side having a plurality of medical supply retaining structures comprising at least one of a pocket and a bungee cord retaining system.

15. The ballistics vest of claim 14, wherein the first and second medical kits are each comprised of a first end portion having an elongate strap attached at one end thereto, the elongate strap having a first section of hook or loop tape attached to a back side thereof and a front side of the end portion having a second section of hook or loop tape attached thereto and configured for selective attachment to the first section of hook or loop tape.

16. The ballistics vest of claim 14, wherein the elongate fabric panel is configured to be folded in half to form a folded end with the plurality of medical supply retaining structures positioned on an inside of the elongate fabric panel when folded.

17. The ballistics vest of claim 16, wherein the first and second medical kits are configured to be inserted with the folded end first into the elongate pouch.

18. The ballistics vest of claim 17, wherein the first grasping strap of the first medical kit is attached to a second end portion of the elongate fabric panel of the first medical kit and the second grasping strap of the second medical kit is attached to a second end portion of the elongate fabric panel of the second medical kit.

* * * * *